United States Patent
Assmus et al.

(10) Patent No.: US 10,588,685 B2
(45) Date of Patent: Mar. 17, 2020

(54) ELECTROSURGICAL GENERATOR

(71) Applicant: OLYMPUS WINTER & IBE GMBH, Hamburg (DE)

(72) Inventors: Ilja Assmus, Werder (DE); Stefan Schiddel, Potsdam (DE); Andreas Karrasch, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 191 days.

(21) Appl. No.: 15/556,184

(22) PCT Filed: Mar. 3, 2016

(86) PCT No.: PCT/EP2016/054544
§ 371 (c)(1),
(2) Date: Sep. 6, 2017

(87) PCT Pub. No.: WO2016/142266
PCT Pub. Date: Sep. 15, 2016

(65) Prior Publication Data
US 2018/0042660 A1    Feb. 15, 2018

(30) Foreign Application Priority Data
Mar. 6, 2015 (DE) .......... 10 2015 204 127

(51) Int. Cl.
*A61B 18/12* (2006.01)
*H02M 7/48* (2007.01)

(52) U.S. Cl.
CPC .......... *A61B 18/1206* (2013.01); *H02M 7/48* (2013.01); *A61B 2018/126* (2013.01);
(Continued)

(58) Field of Classification Search
CPC ........ A61B 2018/0066; A61B 2018/16; A61B 2018/1286; A61B 18/1206; H03G 1/00; H02M 2007/4818; Y02B 70/1441
See application file for complete search history.

(56) References Cited

U.S. PATENT DOCUMENTS

| 4,888,821 A | 12/1989 | Hamp, III et al. |
| 5,438,302 A * | 8/1995 | Goble .................... A61B 18/12 |
| | | 331/117 FE |

(Continued)

FOREIGN PATENT DOCUMENTS

| CN | 102215768 A | 10/2011 |
| CN | 103025259 A | 4/2013 |

(Continued)

OTHER PUBLICATIONS

May 20, 2016 Search report issued in International Patent Application No. PCT/EP2016/054544.

(Continued)

*Primary Examiner* — Michael F Peffley
(74) *Attorney, Agent, or Firm* — Oliff PLC

(57) ABSTRACT

An electrosurgical generator, which has a high-voltage DC power supply unit and a resonant circuit connected thereto. The resonant circuit has an output transformer, the primary winding of which is part of the resonant circuit and the secondary winding of which is connected to connections for an electrosurgical instrument. The resonant circuit is furthermore connected to an actuation circuit, which is configured to periodically emit actuation pulses for the purpose of exciting the resonant circuit using the resonant frequency thereof. The actuation circuit includes a synchronization unit, which is connected to the resonant circuit, and includes at least one gradient detector and is configured to synchro- (Continued)

nize actuation pulses with a reversal point of the voltage profile of the voltage in the resonant circuit.

8 Claims, 10 Drawing Sheets

(52) U.S. Cl.
CPC ............ *A61B 2018/1286* (2013.01); *H02M 2007/4818* (2013.01); *Y02B 70/1441* (2013.01)

(56) References Cited

U.S. PATENT DOCUMENTS

| | | | |
|---|---|---|---|
| 8,864,756 B2 | 10/2014 | Strauss | |
| 2012/0098351 A1* | 4/2012 | Ross | A61B 18/1233 307/104 |
| 2014/0276754 A1* | 9/2014 | Gilbert | A61B 18/18 606/33 |
| 2017/0367751 A1 | 12/2017 | Ruddenklau et al. | |

FOREIGN PATENT DOCUMENTS

| | | |
|---|---|---|
| CN | 104042335 A | 9/2014 |
| DE | 102008039884 A1 | 3/2010 |
| EP | 1080694 A1 | 3/2001 |
| EP | 2777582 A1 | 9/2014 |
| JP | H08-512229 A | 12/1996 |
| JP | 2014-100583 A | 6/2014 |
| WO | 95/02369 A1 | 1/1995 |

OTHER PUBLICATIONS

May 20, 2016 Written Opinion issued in International Patent Application No. PCT/EP2016/054544.

Dec. 17, 2015 Office Action issued in German Patent Application No. 102015204127.1.

May 5, 2019 Office Action issued in Chinese Patent Application No. 201680011087.X.

May 5, 2019 Search Report issued in Chinese Patent Applicaltion No. 201680011087.X.

* cited by examiner

ELECTROSURGICAL GENERATOR

The invention relates to an electrosurgical generator to which an electrosurgical instrument can be connected or is connected.

Electrosurgical generators of this kind typically have a resonant circuit and an output transformer as well as a DC power supply unit in order to energize the resonant circuit. This is dependent on the fact that the resonant circuit is energized using DC pulses in a clocked manner in such a way that the DC pulses are fed in synchronously with the voltage profile of the voltages in the resonant circuit. The DC pulses are typically generated with a fixed frequency and fed into the resonant circuit. In this case, said frequency should correspond to the resonant frequency of the resonant circuit, given a predetermined load. A DC power supply unit of this kind and the resonant circuit must therefore be tuned to one another, if necessary manually, and in certain circumstances must also be retuned at a later stage.

Even in the case of precise tuning, the excitation frequency may match only the resonant frequency, when the actual load corresponds to the predetermined load, since the resonant frequency of the resonant circuit likewise changes when the load changes.

This leads to a situation where the excitation frequency no longer corresponds to the resonant frequency of the resonant circuit when the load is changed. This can lead to power losses and distortions in the signal profile.

The invention is based on the object of providing an electrosurgical generator, which achieves synchronization of DC pulses as control pulses for the purpose of exciting the resonant circuit using the resonant frequency thereof.

Said object is achieved in accordance with the invention by an electrosurgical generator, which has a high-voltage DC power supply unit and a resonant circuit connected thereto. The resonant circuit has an output transformer, the primary winding of which is part of the resonant circuit and the secondary winding of which is connected to connections for an electrosurgical instrument. The resonant circuit is furthermore connected to an actuation circuit, which is configured to periodically emit actuation pulses for the purpose of exciting the resonant circuit using the resonant frequency thereof. In accordance with the invention, the actuation circuit comprises a synchronization unit, which is connected to the resonant circuit, comprises at least one gradient detector and is configured to synchronize actuation pulses with a reversal point of the voltage profile of the voltage in the resonant circuit. Here, the synchronization unit is configured to determine a respective reversal point of the voltage profile of the voltage in the resonant circuit by means of the gradient detector. Here, the gradient detector is configured to detect a change in the gradient direction of the voltage profile of the voltage in the resonant circuit and to emit a synchronization signal that causes the actuation circuit to trigger an actuation pulse for the resonant circuit.

An electrosurgical generator of this kind makes manual tuning of the high-voltage DC power supply unit to the resonant circuit superfluous, because the emission of the actuation pulses by the synchronization unit is automatically synchronized with the voltage profile of the voltages in the resonant circuit.

The gradient detector preferably has a differentiation circuit, which is configured to generate a derivative signal that corresponds to the derivative of the voltage profile of the voltage in the resonant circuit. The differentiation circuit is preferably connected to a zero crossing detector, which is configured to detect a respective zero crossing of the derivative signal and subsequently to trigger the synchronization signal. A zero crossing of the derivative signal corresponds to a change in the gradient direction of the voltage profile of the voltage in the resonant circuit, with the result that the synchronization signal generated by the zero crossing detector consistently follows the identification of a reversal point of the voltage profile of the voltages in the resonant circuit.

Furthermore, the gradient detector is preferably configured to sample the voltage profile of the frequency in the resonant circuit using a fixed sampling rate, which is a multiple of the frequency of the voltage profile of the voltage in the resonant circuit, and to compare consecutive sampled voltage values with one another. In this case, the gradient detector is preferably configured to perform the comparison of the respective consecutive sampled voltage values by forming the difference and to trigger the synchronization signal when the sign of the difference changes.

Particularly preferred is an electrosurgical generator, in which the gradient detector comprises a resonant crossing detector, which is configured to detect a zero crossing of the voltage profile of the voltage in the resonant circuit.

In an electrosurgical generator of this kind, the synchronization unit is preferably configured to determine a respective reversal point of the voltage profile of the voltages in the resonant circuit by means of the resonant zero crossing detector and the gradient detector and to emit the synchronization signal.

In a particularly preferred embodiment variant, in which the gradient detector is configured to sample the voltage profile of the voltage in the resonant circuit using a sampling rate, it is preferable for the synchronization unit to be configured, when the sign of the difference of the consecutive sampled voltage values changes, to trigger the synchronization signal in accordance with a zero crossing previously detected by the resonant zero crossing detector.

The differentiation circuit preferably has a differential amplifier, which is connected as a differential element by means of an RC element and to which the voltage u in the resonant circuit is fed as input signal and which delivers the derivative signal as output signal.

The invention will now be described in more detail on the basis of an exemplary embodiment with reference to the figures, in which.

Figure 1:
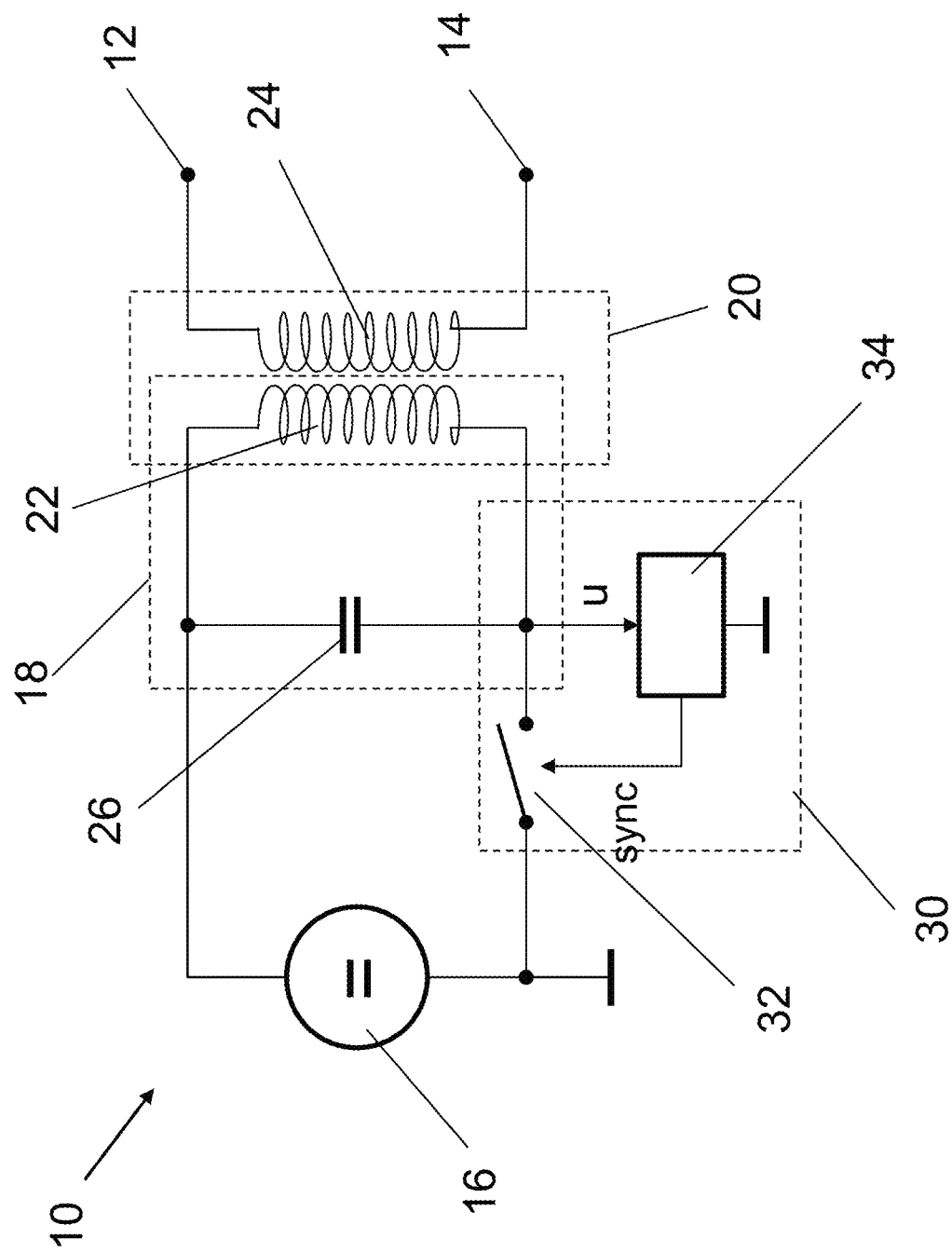
FIG. 1 shows some essential components of an electrosurgical generator according to the invention.

FIG. 1 shows the essential components of an electrosurgical generator 10 having two connections 12 and 14, to which an electrosurgical instrument can be connected or can also be permanently connected. The electrosurgical generator 10 is configured to provide a high-frequency AC voltage at the connections 12 and 14, said high-frequency AC voltage being suitable for coagulation, ablation or for electrosurgically cutting body tissue, for example.

The electrosurgical generator 10 comprises a high-voltage DC power supply unit 16, a resonant circuit 18 and an output transformer 20. The output transformer has a primary winding 22 and a secondary winding 24. The primary winding 22, together with a capacitor 26, forms the resonant circuit 18. The primary winding 22 of the output transformer 20 is therefore simultaneously a coil in the resonant circuit 18. The connections 12 and 14 are connected to the secondary winding 24 of the output transformer 20. In some circumstances, the secondary winding 24 can have a plurality of taps, with the result that the connections 12 and/or 14, in some circumstances, can be connected to respectively suitable taps on the secondary winding 24 by means of a switch or a switching matrix, in order to provide different output voltages.

Furthermore, the electrosurgical generator 10 has an actuation circuit 30, which is connected to the high-voltage DC power supply unit 16 and the resonant circuit 18 and which is configured to periodically emit actuation pulses for the purpose of exciting the resonant circuit 18 using the resonant frequency thereof. For this purpose, the actuation circuit 30 has a switch 32, which can be realized by any desired suitable electrical component, for example a transistor. In order to actuate the switch 32 synchronously with the voltage profile of the voltage in the resonant circuit, a synchronization unit 34 is provided, which is connected to the resonant circuit 18, in order to tap the voltage u in the resonant circuit 18 and, depending on the voltage profile of said voltage u, to generate and output a synchronization signal sync and to actuate the switch 32 using said synchronization signal sync in such a way that said switch closes in a manner actuated by the synchronization signal sync and thus feeds a respective actuation pulse into the resonant circuit 18.

Figure 2:
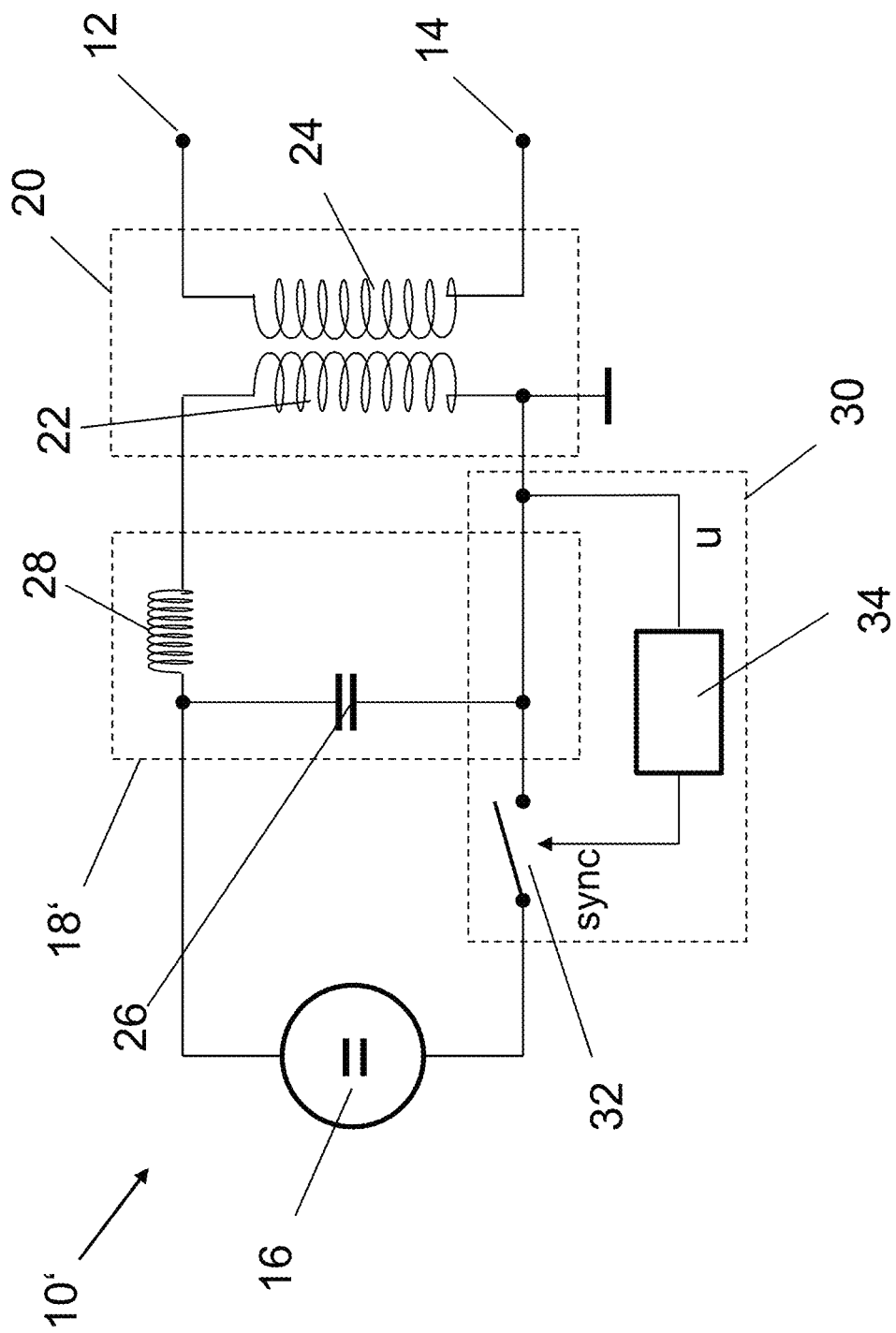
FIG. 2 shows some essential components of an alternative variant of an electrosurgical generator according to the invention.

FIG. 2 shows an alternative variant of an electrosurgical generator 10', which differs from the electrosurgical generator 10 from FIG. 1 in that the resonant circuit 18' has, in addition to a capacitor 26, a resonant circuit coil 28, which, in the illustrated exemplary embodiment, is connected in series with the primary winding 22 of the output transformer 20, with the result that the resonant frequency of the resonant circuit 18' is determined by the resonant circuit coil 28, the primary winding 22 and the capacitance (the capacitor) 26. With the exception of details of the grounding, the design of the electrosurgical generator 10' is otherwise similar to the design of the electrosurgical generator 10 from FIG. 1.

Figure 3:
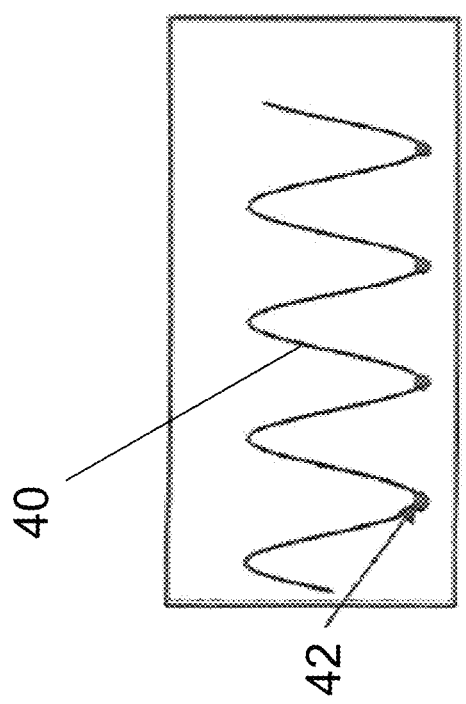
FIG. 3 shows an illustration of a resonance that represents the voltage profile of the voltages in the resonant circuit and the synchronization times for the actuation pulses are marked therein.

Ideally, the actuation pulses are triggered synchronously with a respective positive or negative maximum of the AC voltage in the resonant circuit 18. In a respective positive or negative maximum of the AC voltage, the gradient of the voltage profile of the AC voltage is 0; the voltage profile is reversed at that point, that is to say that the actuation pulses are to be synchronized with a respective (positive or negative) reversal point 42 of the voltage profile 40. This is illustrated in FIG. 3.

Figure 4:
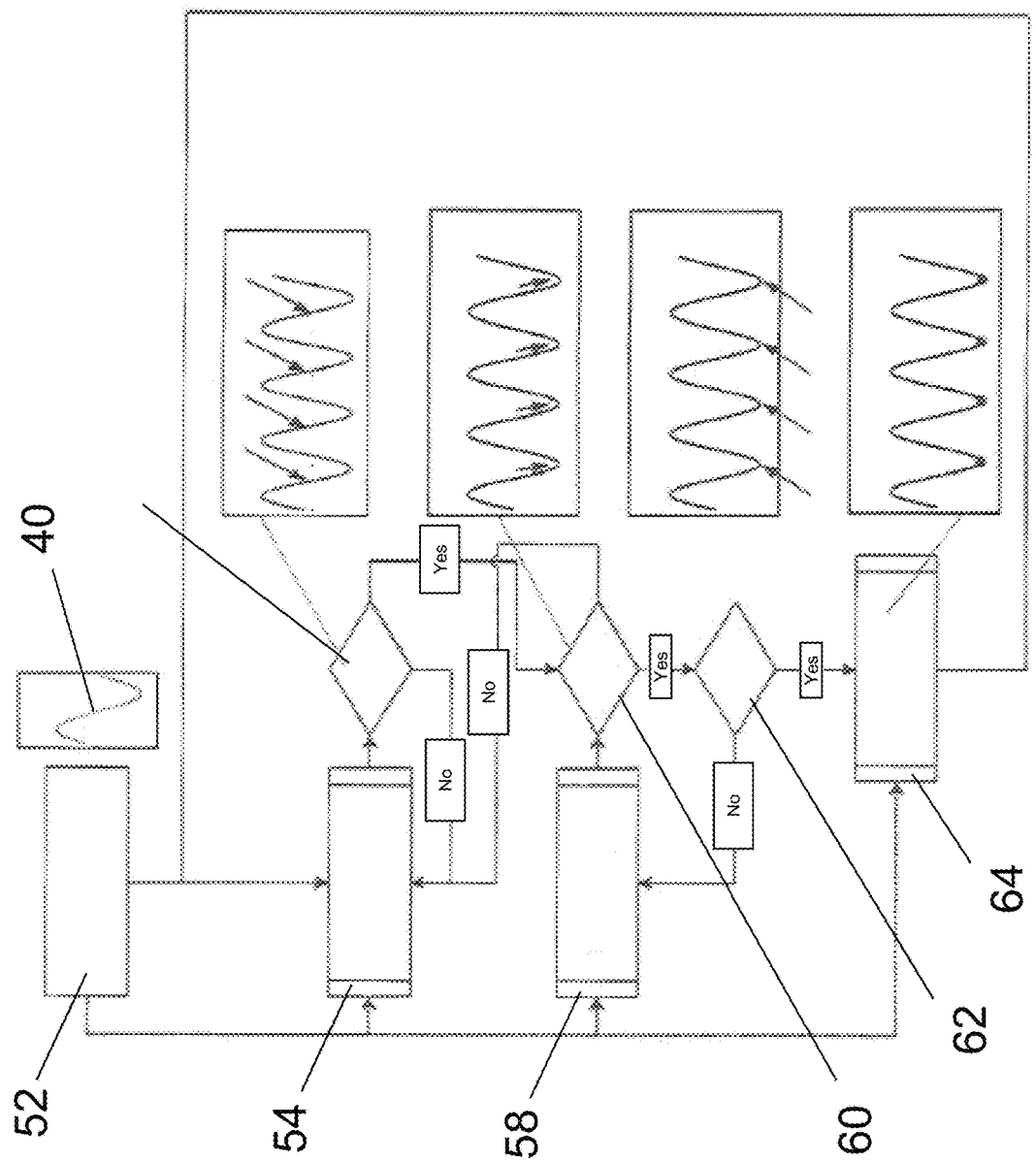
FIG. 4 shows a flow diagram for the purpose of illustrating a possible mode of operation of a synchronization unit according to the invention for an electrosurgical generator according to the invention.

FIG. 4 uses a flow diagram to illustrate a variant of how the synchronization unit 34 detects a respective reversal point 42 of the voltage profile 40 of the voltage in the resonant circuit 18 and subsequently generates a respective synchronization signal. The process illustrated in FIG. 4 is triggered for the purpose of generating a synchronization signal and generating an actuation pulse as a follow-up pulse to a preceding actuation pulse by a first actuation pulse (starting pulse) 52. A resonant zero crossing detector 54 is started using the starting pulse 52, said resonant zero crossing detector being configured to detect either a positive or a negative zero crossing of the voltage profile of the voltage in the resonant circuit. In the exemplary embodiment, the resonant zero crossing detector 54 is configured to detect a zero crossing from positive to negative (negative zero crossing) of the voltage profile of the voltage of the resonant circuit 18. If a zero crossing of this kind is detected, the resonant zero crossing detector 54 generates an output signal (yes).

In parallel therewith, a gradient detector 58 determines a respective gradient of the voltage profile of the voltage in the resonant circuit 18 and checks (step 60) whether said gradient is less than zero. If this is the case, the gradient detector 58 then waits (step 62) until the gradient is zero. As soon as this is the case, a reversal point of the voltage profile of the voltage in the resonant circuit 18 is present and a synchronization signal (yes) is triggered and a follow-up pulse (64) is triggered.

The process depicted in FIG. 4 can therefore also be summarized as follows: after a starting pulse 52 has occurred, a resonant zero crossing is firstly determined by means of a resonant zero crossing detector 54. Since the synchronization signal and hence the next actuation pulse (follow-up pulse 64) are meant to occur out the "lower" reversal point (270°) the voltage profile from the voltage in the resonant circuit 18, but the sinusoidal voltage profile only has two zero crossings, in step 60 the gradient detector 58 checks, in parallel or subsequently, whether the gradient of the voltage profile is negative. If this is the case (60), then step 62 waits until the next reversal point of the voltage profile of the voltage in the resonant circuit 18 has been reached, at which reversal point the next actuation pulse (follow-up pulse) should be triggered. Said reversal point is determined in step 62 by virtue of the fact that a check is carried out as to when the gradient of the voltage profile of the voltage in the resonant circuit 18 is zero. If this is the case, the synchronization signal and hence the next actuation pulse as the follow-up pulse can be triggered in step 64. The process can then start all over again.

Figure 5:
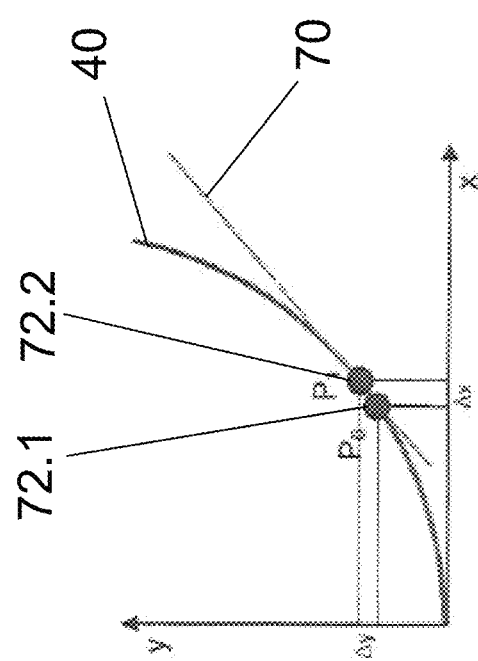
FIG. 5 shows an illustration for the purpose of explaining the comparison of respectively consecutive sampled voltage values.

FIG. 5 illustrates how the gradient detector 58 can determine the gradient 70 of the sinusoidal voltage profile from adjacent sampling values (voltage values) 72.1 and 72.2. When the voltage in the resonant circuit 18 is sampled using a fixed sampling rate, the consecutive voltage values 72.1 and 72.2 have a time interval $\Delta X$ and—if the instantaneous gradient of the voltage profile is not zero—a difference $\Delta Y$. The gradient of the $m_t$ tangent 70 in the voltage profile 40 represents the instantaneous gradient of the voltage profile. When the sampling rate is sufficiently high (that is to say that $\Delta x$ is sufficiently small), the gradient $m_t$ of the tangent 70 corresponds to the gradient of a secant through the points P0 and P1, which can be determined from the sampling values 72.1 and 72.2 and, given a constant ΔX (that is to say a constant sampling rate), is described by the difference ΔY of the sampling values. The accuracy of the tangent gradient $m_t$ depends on how small ΔX is.

Figure 6:
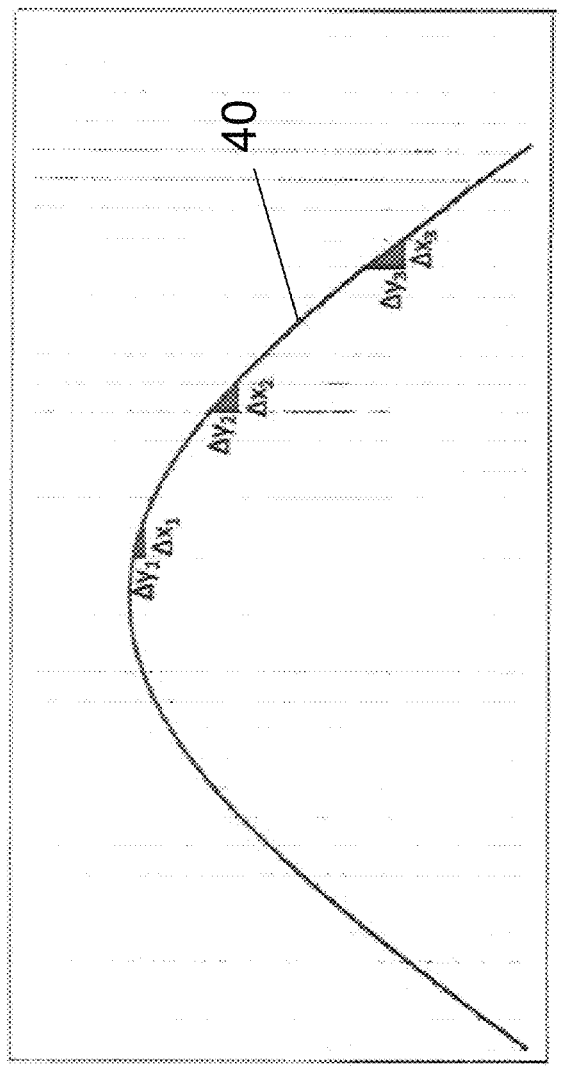
FIG. 6 shows a section of a voltage profile and an illustration of different gradients thereof.

FIG. 6 illustrates how the gradient can be described solely by a respective ΔY, when ΔX is always constant. FIG. 5 therefore illustrates that, given a constant ΔX, the gradient of the voltage profile of the voltage in the resonant circuit 18 is clearly described at each instant by ΔY. In accordance therewith, the difference ΔY of two consecutive sampling values of the voltage in the resonant circuit 18 represents the gradient of the respective voltage profile, provided that the sampling rate is constant and large enough that the reversal point (gradient $m_t$=0) can be acknowledged.

Figure 7:
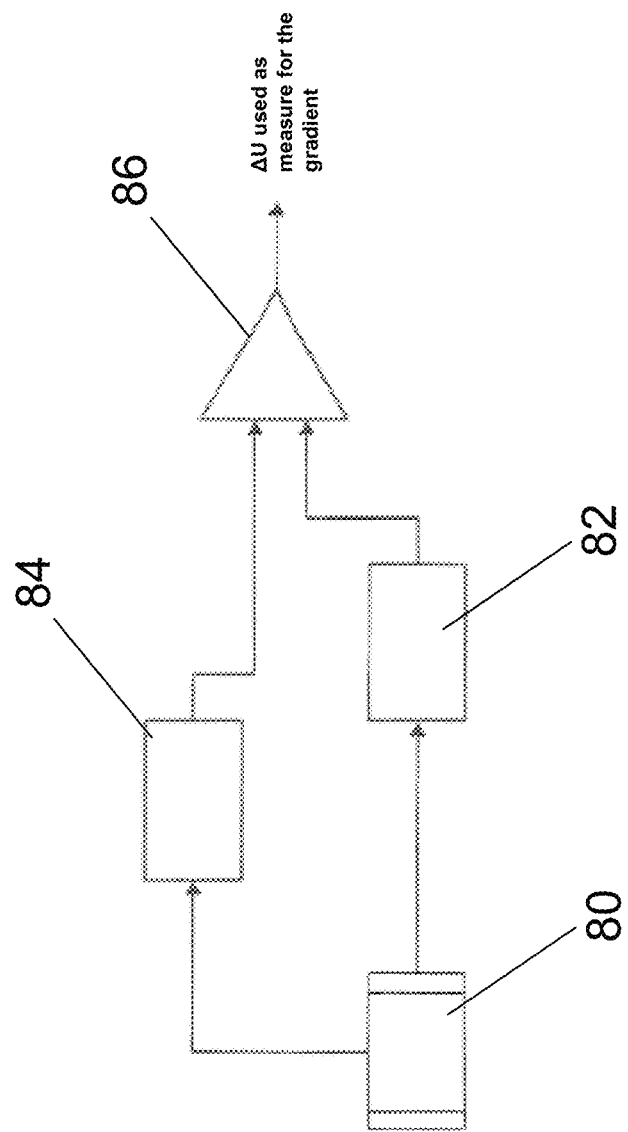
FIG. 7 shows constituent parts of an embodiment variant of a synchronization unit according to the invention for the purpose of determining a respective gradient of the voltage profile by forming the difference of sampling values.

FIG. 7 illustrates the diagram for determining ΔY as a measure for the gradient $m_t$. A current sampling value 82 with a preceding sampling value 84 is added to a differential amplifier 86 in time with the sampling rate 80. This forms the difference between a respective current sampling value and a respective preceding sampling value. The voltage at the output of the differential amplifier 86 corresponds to said difference. If the voltage at the output of the differential amplifier 86 is equal to zero, this means that the gradient of the voltage profile of the voltage in the resonant circuit 18 has also reached a vertex point and hence a reversal point. The reversal point of the voltage profile of the voltage in the resonant circuit 18 can therefore be determined by comparing the consecutive sampling values (voltage values) of the voltage in the resonant circuit and a synchronization signal can then be generated when said difference is zero, undershoots a threshold value close to zero or when the sign of two consecutively determined differences changes.

The gradient of the voltage profile 40 of the voltage in the resonant circuit 18 can be formed by forming the time derivative of the voltage profile. A measure of the gradients of a sinusoidal curve is known to be the cosine thereof:

$$\frac{d}{dt}\sin(\alpha) = \cos(\alpha)$$

The time derivative of a sinusoidal voltage profile is therefore cosinusoidal and it results that the time derivative of the voltage profile in the resonant circuit 18 at the reversal points of the voltage profile (α=90° and α=270°) is zero because the cosine at the inflection points of the sine function is equal to zero.

Figure 8:
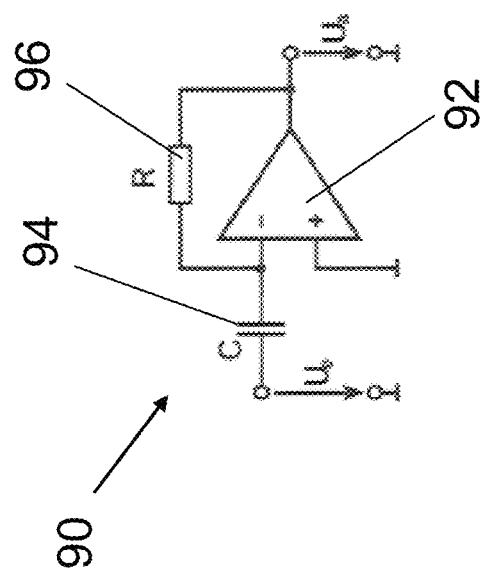
FIG. 8 shows an illustration of a differential element for a differentiation circuit as part of a gradient detector for a synchronization unit according to the invention.

FIG. 8 illustrates that the sinusoidal voltage in the resonant circuit 18 can be fed as input voltage $U_e$ to a differentiation circuit 90, at the output of which a voltage $U_a$ is then applied, the profile of which corresponds to the time derivative of the voltage profile 40 of the voltage in the resonant circuit 18 and therefore forms a derivative signal.

The differentiation circuit 90 has a differential amplifier 92, the non-inverted input of which is connected to ground in the exemplary embodiment. A capacitor 94 is connected upstream of the inverting input of the differential amplifier 92 and an ohmic resistor 96 is connected in parallel with the differential amplifier 92, between the inverting input of the differential amplifier 92 and the output thereof. The capacitor 94 and the ohmic resistor 96 form an RC element, which can be tuned to the expected frequency range, that is to say the resonant frequency of the resonant circuit. The output voltage $U_a$ of the differentiation circuit 90 is zero when the input voltage $U_e$ and hence the voltage profile of the voltage in the resonant circuit 18 reaches the maximum value or the minimum value.

It should be expected, specifically on account of component differences in the resonant circuit 18, that the employed RC element the differentiation circuit 90 has an influence on the amplitude of the output voltage $U_a$ at the output of the differential amplifier 92. This has the result that the output voltage $U_a$ possibly does not reach the expected maximum amplitude thereof. However, since it depends on the detection of the reversal points of the voltage profile of the voltage in the resonant circuit 18, the maximum value of the output voltage $U_a$ of the differentiation circuit 90 is not important, since the output voltage $U_a$ is zero in the reversal points of the voltage profile of the voltage in the resonant circuit 18. That is to say that it suffices for a zero crossing detector to be connected downstream of the differentiation circuit 90, said zero crossing detector generating the synchronization signal at each (either positive or negative) zero crossing of the output voltage $U_a$. The differentiation circuit 90 and a zero crossing detector 98 of this kind therefore represent a vertex point detector 100. This is illustrated in FIG. 9.

Figure 9:
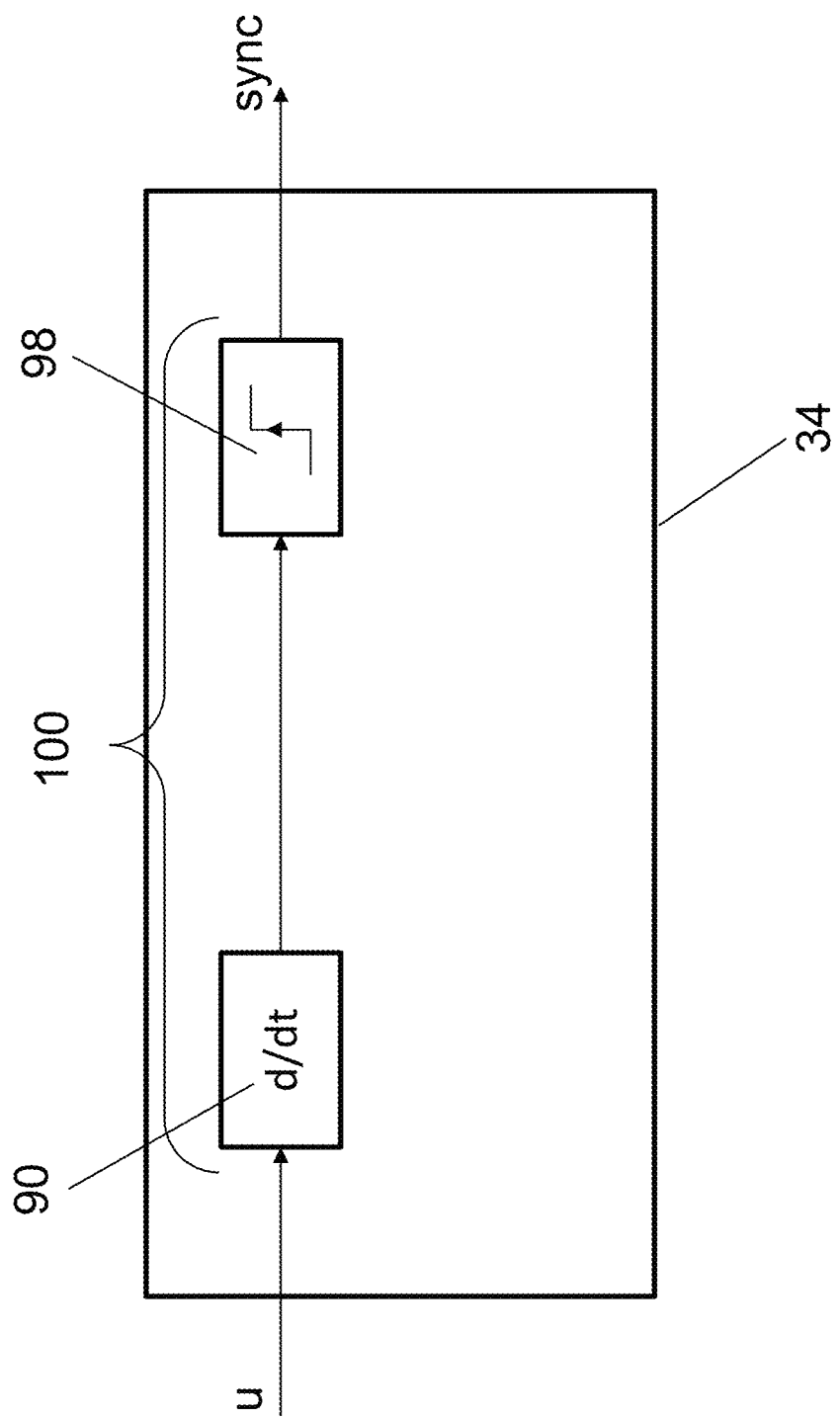
FIG. 9 shows a schematic illustration of the main components of a first variant of a synchronization unit.

FIG. 9 shows an embodiment variant of a synchronization unit 34, which has a vertex point detector 100, which is formed of a differentiation circuit 90 and a zero crossing detector 98 connected downstream thereof.

Figure 10:
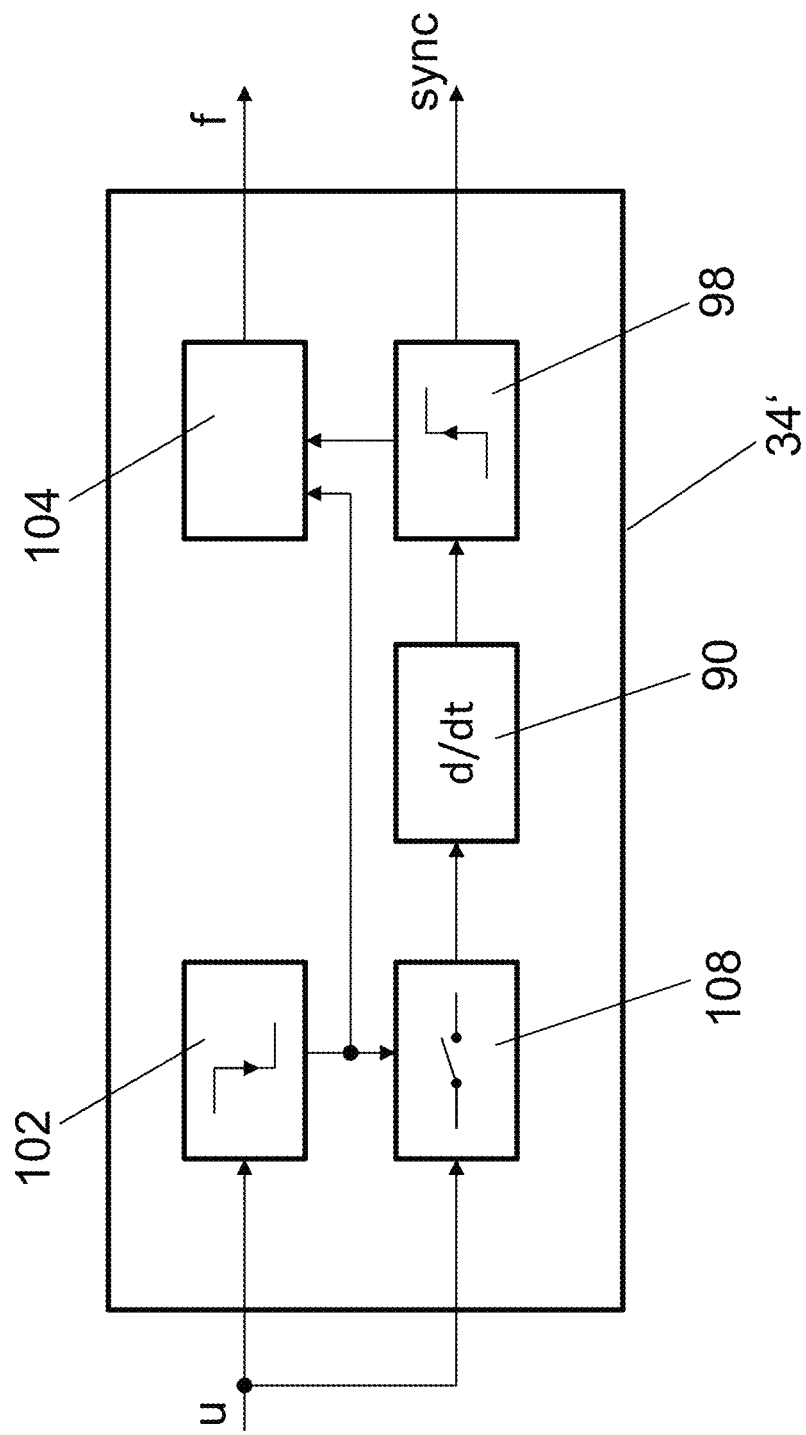
FIG. 10 shows a schematic illustration of the most important components of a second variant of the synchronization unit.

In a further embodiment variant depicted in FIG. 10, the synchronization unit 34' can also have, in addition to the vertex point detector 100, a resonant zero crossing detector 102 connected upstream thereof, the input signal of which is the voltage or the voltage profile of the voltage in the resonant circuit 18 and which detects a crossing of the voltage profile of the voltage in the resonant circuit 18 from positive to negative values (negative zero crossing) and subsequently outputs an output signal. Said output signal is fed, on the one hand, to a frequency detector 104 and, on the other hand, to a switch 108, which is connected upstream of the vertex point detector 100 and the differentiation circuit 90 thereof. In the case of a respective negative zero crossing of the voltage profile of the voltage in the resonant circuit 18, the switch 108 is closed by the output signal of the resonant zero crossing detector 102 and hence the voltage in the resonant circuit 18 is fed to the input of the differentiation circuit 90. The mode of operation of the synchronization unit 34' in FIG. 10 therefore corresponds exactly to the procedure illustrated in FIG. 4.

The input value of the synchronization unit 34' from FIG. 10 is therefore the voltage u in the resonant circuit 18. The output values of the synchronization unit 34' are, in addition to the synchronization signal sync, a signal f, which represents the frequency of the voltage profile of the voltage in the resonant circuit 18.

LIST OF REFERENCE SYMBOLS

Electrosurgical generator 10
Connections 12, 14
High-voltage DC power supply unit 16
Resonant circuit 18, 18'
Output transformer 20
Primary winding 22
Secondary winding 24
Capacitor 26, 94
Resonant circuit coil 28
Actuation circuit 30
Switch 32, 108

Synchronization unit 34, 34'
Voltage profile 40
Reversal point 42
Starting pulse 52
Resonant zero crossing detector 54, 102
Gradient detector 58
Follow-up pulse 64
Tangent, gradient 70
Sampling value, voltage value 72.1, 72.2
Sampling rate 80
Current sampling value 82
Preceding sampling value 84
Differential amplifier 86, 92
Differentiation circuit 90
Resistor 96
Zero crossing detector 98
Vertex point detector 100
Frequency detector 104

The invention claimed is:

1. An electrosurgical generator comprising:
a high-voltage DC power supply; and
a resonant circuit that is connected to the high-voltage DC power supply, the resonant circuit having an output transformer including a primary winding and a distinct secondary winding electrically connected to connections for an electrosurgical instrument, the primary winding of the output transformer being formed as part of the resonant circuit, the secondary winding being isolated from the primary winding, the resonant circuit being electrically connected to an actuation circuit configured to periodically emit actuation pulses configured to excite the resonant circuit using a resonant frequency of the resonant circuit, wherein:
the actuation circuit includes a synchronization unit electrically connected to the resonant circuit, the synchronization unit includes at least one gradient detector, and the synchronization unit is configured to synchronize actuation pulses with a reversal point of a voltage profile of a voltage in the resonant circuit,
the synchronization unit is configured to determine the respective reversal point of the voltage profile of the voltage in the resonant circuit using of the gradient detector, and
the gradient detector is configured to detect a change in a gradient direction of the voltage profile of the voltage in the resonant circuit and to emit a synchronization signal that causes the actuation circuit to trigger an actuation pulse for the resonant circuit.

2. The electrosurgical generator as claimed in claim 1, wherein the gradient detector includes a differentiation circuit configured to generate a derivative signal that corresponds to a derivative of the voltage profile of the voltage in the resonant circuit.

3. The electrosurgical generator as claimed in claim 2, wherein the synchronization unit includes a zero crossing detector connected downstream of the differentiation circuit, and the zero crossing detector is configured to detect a respective zero crossing of the derivative signal and subsequently to trigger the synchronization signal.

4. The electrosurgical generator as claimed in claim 1, wherein the gradient detector is configured to sample the voltage profile of the voltage in the resonant circuit using a fixed sampling rate, which is a multiple of a frequency of the voltage profile of the voltage in the resonant circuit, and the gradient detector is configured to compare consecutive sampled voltage values with one another.

5. The electrosurgical generator as claimed in claim 4, wherein the gradient detector is configured to perform the comparison of the respective consecutive sampled voltage values by forming the difference.

6. The electrosurgical generator as claimed in claim 5, wherein the synchronization unit is configured to trigger the synchronization signal when a sign of the difference changes.

7. The electrosurgical generator as claimed in claim 1, wherein
the synchronization unit includes a resonant zero crossing detector configured to detect a zero crossing of the voltage profile of the voltage in the resonant circuit, and
the synchronization unit is configured to determine the respective reversal point of the voltage profile of the voltage in the resonant circuit in response to the resonant zero crossing detector using the gradient detector and the synchronization unit is configured to emit the synchronization signal.

8. The electrosurgical generator as claimed in claim 2, wherein the differentiation circuit has a differential amplifier connected as a differential element by an RC element to which the voltage of the resonant circuit is fed as an input signal and which delivers the derivative signal as an output signal.

* * * * *